United States Patent [19]

Yamaguchi

[11] Patent Number: 5,118,714

[45] Date of Patent: Jun. 2, 1992

[54] AQUEOUS EXTRACT FROM PITTOSPORACEAE EFFECTIVE FOR TREATING DIABETES AND LIVER DYSFUNCTION

[76] Inventor: Akeomi Yamaguchi, 44-3, Sasahara, Kokubunjimachi, Shimotsuga-Gun, Tochigi-Prefecture, Japan

[21] Appl. No.: 705,396

[22] Filed: May 24, 1991

Related U.S. Application Data

[63] Continuation-in-part of Ser. No. 409,824, Sep. 20, 1989, abandoned.

[30] Foreign Application Priority Data

Oct. 3, 1988 [JP] Japan .............................. 63-247390

[51] Int. Cl.⁵ .............................................. A61K 35/78
[52] U.S. Cl. .................................... 514/783; 424/195.1
[58] Field of Search ....................... 424/195.1; 514/783

[56] References Cited

PUBLICATIONS

Steinmetz, E. F., Codex Vegetabilis, 1957, Amsterdam #859.

Primary Examiner—Ronald W. Griffin
Assistant Examiner—Ralph Gitomer
Attorney, Agent, or Firm—Kane, Dalsimer, Sullivan, Kurucz, Eisele and Richard

[57] ABSTRACT

Disclosed is a water-soluble extract obtained from Pittosporaceae and effective for the treatment for diabetes and liver dysfunctions, which exhibits the following characteristic absorption in the infrared region of the spectrum: strong absorption bands at 1050–1070 $cm^{-1}$, 1620 $cm^{-1}$, 2950 $cm^{-1}$, and 3450 $cm^{-1}$, and relatively strong absorption bands at 520 $cm^{-1}$, 780 $cm^{-1}$, 1250 $cm^{-1}$, 1320 $cm^{-1}$, 1380–1440 $cm^{-1}$ (doublet), 1735 $cm^{-1}$ and 2850 $cm^{-1}$.

2 Claims, 2 Drawing Sheets

AQUEOUS EXTRACT FROM PITTOSPORACEAE EFFECTIVE FOR TREATING DIABETES AND LIVER DYSFUNCTION

CROSS-REFERENCE TO RELATED APPLICATION

This application is a Continuation-In-Part application of U.S. patent application Ser. No. 409,824 filed Sep. 20, 1989 now abandoned.

BACKGROUND OF THE INVENTION

1. Field of the Invention

The present invention relates to a water-soluble extract from Pittosporaceae effective for the treatment of diabetes and liver complaints, and a process for preparing the same.

2. Brief Description of the Prior Art

Vitamin $B_{12}$ called cobalamin is an animal protein factor. In the past cobalamin has been extracted in extremely small quantities from animals, but now can be extracted from microorganisms. The demand for cobalamin is increasing.

SUMMARY OF THE INVENTION

It is an object of the present invention to provide Vitamin $B_{12}$ that is, cobalamin, more easily and effectively.

It is another object of the present invention to provide an extract from Pittosporaceae effective for the treatment of diabetes and liver dysfunctions.

According to an aspect of the present invention, a water-soluble extract obtained from Pittosporaceae and effective for the treatment for diabetes and liver complaints, which mainly contains vitamin $B_{12}$, vitamin $B_2$, saponin and tannin, exhibits the following characteristic absorption in the infrared region of the spectrum: strong absorption bands at $1050 - 1070$ $cm^{-1}$, $1620$ $cm^{-1}$, $2950$ $cm^{-1}$ and $3450$ $cm^{-1}$; and relatively strong absorption bands at $520$ $cm^{-1}$, $780$ $cm^{-1}$, $1250$ $cm^{-1}$, $1320$ $cm^{-1}$, $1380-1440$ $cm^{-1}$ (doublet), $1735$ $cm^{-1}$ and $2850$ $cm^{-1}$.

DETAILED DESCRIPTION OF THE INVENTION

The inventor has found that vitamin $B_{12}$ is present in an extract from Pittosporaceae and that the extract is very effective for the treatment of liver dysfunction and diabetes though whether the effectiveness of the extract is caused by the existence of plant vitamin $B_{12}$ or by the existence of other unidentified matters in not known.

According to analysis of the extract in the amount of 10 g as freeze-dried powder, the extract contains 2 μg of vitamin $B_{12}$, 9.5 mg of vitamin $B_2$, 2.5 g of tannin, and other unanalyzable matters such as saponin the quantity of which is not yet measured but very minute.

The extract according to the present invention is obtained from Pittosporaceae, such as Pittosporum glabratum Lindl, Pittosporum oligocarpum Hayata, Pittosporum Tobira Ait, Pittosporum undulatum Vent, and the like, by the following process.

Powder prepared by dehydrating roots, stems, leaves, and the like, of Pittosporaceae is mixed with water, preferably, in the amount several times as much as the amount of powder. The resulting mixture is left for several days, so that the mixture is separated into the two layers of an aqueous solution and a precipitate. The aqueous solution is evaporated to be concentrated under reduced pressure in a boiling state at a temperature of about 40° C. near body temperature. The solution thus concentrated contains an extract. The solution can be powdered by a freeze-dry method which comprises freezing it rapidly to temperatures of $-30°$ C. to $-40°$ C. and drying it slowly to the ordinary temperature by sublimation of water under reduced pressure of 1 to 0.01 mmHg.

Figure 1:
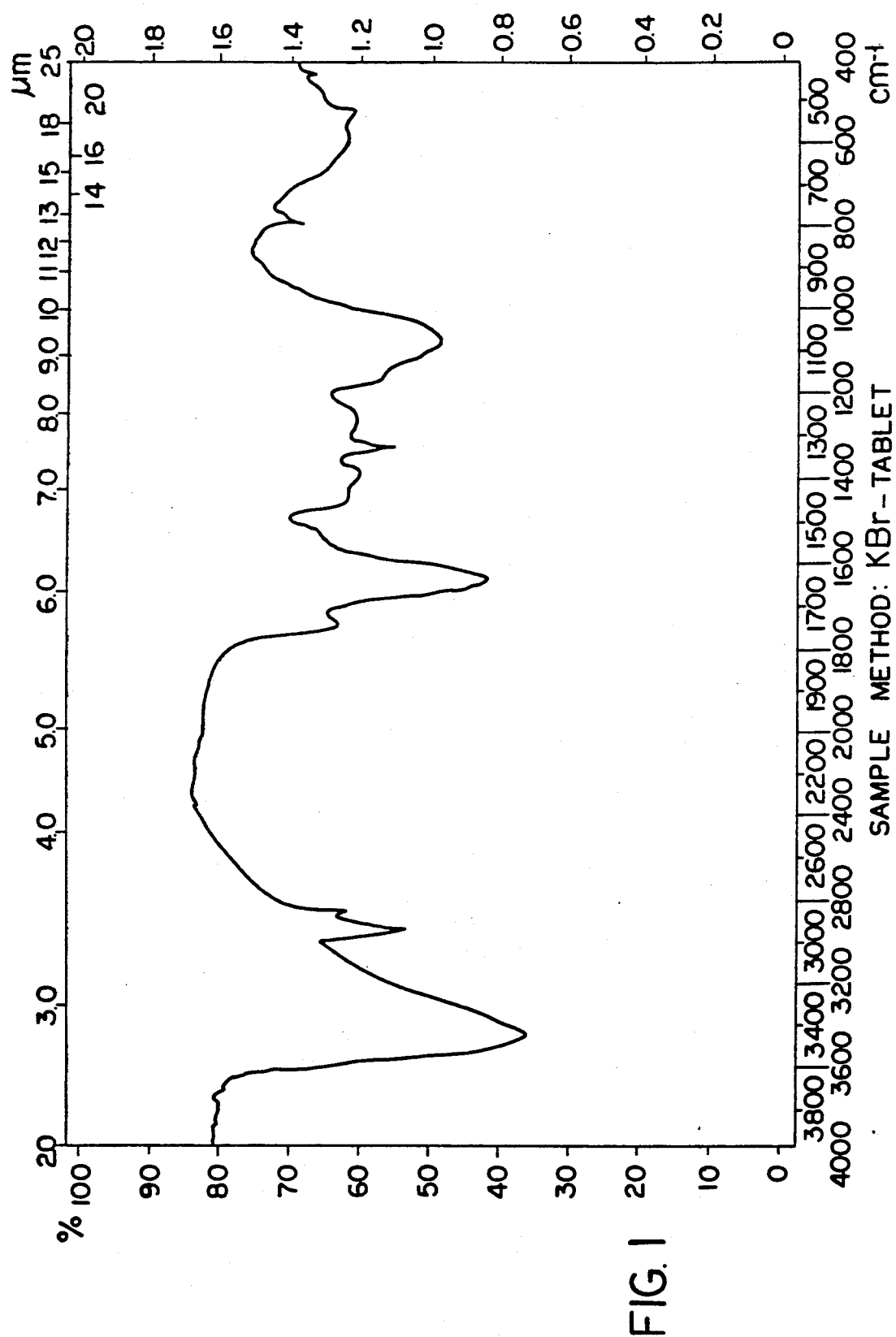
FIG. 1 is a graph showing the infrared absorption spectrum of a powder extract prepared in Example 1 as an embodiment of the present invention.

When the powder-shaped extract dissolved in an equal quantity of water is measured for infrared absorption spectrum analysis, the infrared absorption spectrum as shown in FIG. 1 is obtained.

The spectrum exhibits the following characteristic absorption bands:

strong absorption bands at $1050-1070$ $cm^{-1}$, $1620$ $cm^{-1}$, $2950$ $cm^{-1}$, and $3450$ $cm^{-1}$; and relatively strong absorption bands at $520$ $cm^{-1}$, $780$ $cm^{-1}$, $1250$ $cm^{-1}$, $1320$ $cm^{-1}$, $1380-1440$ $cm^{-1}$ (doublet), $1735$ $cm^{-1}$ and $2850$ $cm^{-1}$.

The extract according to the present invention has the excellent effect beyond expectation as a medicine for diabetes and liver dysfunction.

For use of the extract according to the invention as a medicine, the extract may be used in the form of a solution prepared after the step of concentration under reduced-pressure but before the step of freeze-dry or may be used in the form of a dilution of the solution or, preferably, may be used in the form of powder prepared by freeze-drying the solution. The freeze-dried powder of the extract is soluble in water so that it can be used in the form of an aqueous solution. Further, the freeze-dried powder can be orally administered in the form of a powdered medicine or a tablet medicine prepared by mixing a mass such as lactose.

When, for example, the extract is orally administered as a solution, the oral administration of 2 to 4 doses, each dose of about 100 ml of an extract solution having a concentration between 50 and 600 mg/l, is effective. It is however preferable that the freeze-dried powder is orally administered as a powdered medicine of from a 1/10 extract mixture to a 1/20 extract mixture.

Because the extract according to the present invention is obtained from plants, the toxicity of the extract is very low. When the acute toxicity of the extract was measured by orally administering a 1/10 extract solution to rats, the extract was harmless in a physically allowable range.

The following examples illustrate the invention in more detail.

EXAMPLE 1 (Extraction)

Figure 2A:
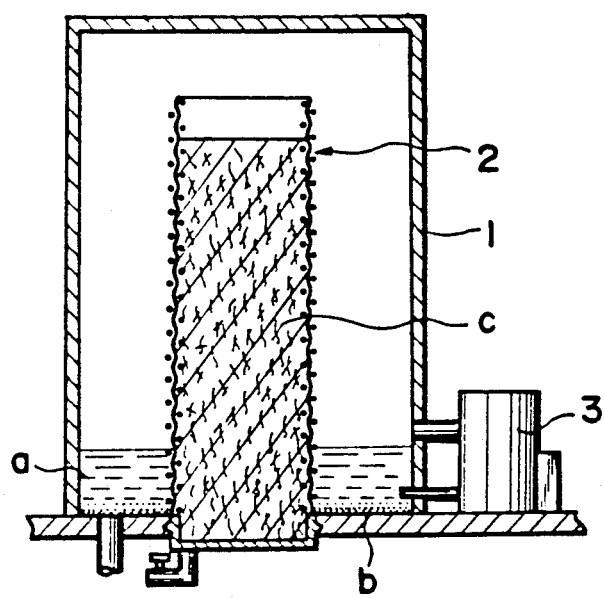
FIGS. 2a and 2b are views showing an extractor employed in the process of extraction described in Example 1.
Figure 2B:
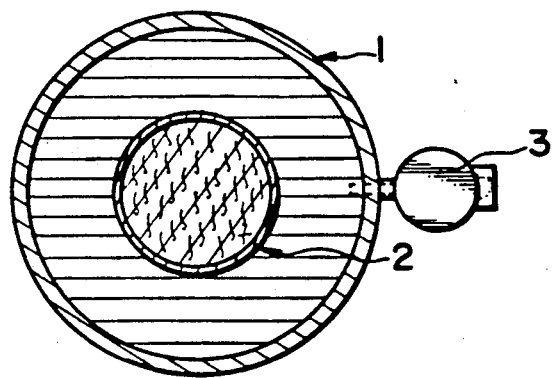

Equal quantities of Pittosporum glabratum Lindl and Pittosporum oligocarpum Hayata were powdered by drying in the shade their leaves for 6 months and their roots and stems for 1 year. In an extractor as described in FIGS. 2a and 2b, 200 g of the powder thus prepared was put in a meshy inner container 2. One liter of water was introduced into a container 1 arranged in the outside of the container 2, so that the powder was entirely immersed in water. The water was heated to be kept at about 40° C. for 5 days. After the 5 days, an aqueous solution layer (a) and a fine-powder precipitate layer (b) taken out of the inner container 2 were observed in the outer container 1. A rough precipitate layer (c) remained in the inner container 2. The layers (b) and (c) were removed so that 850 ml of the aqueous solution layer (a) alone remained in the container. The concentration of the aqueous solution was 15 g/l. The aqueous solution was concentrated at a temperature of about 40° C. under pressure reduced by a vacuum pump 3, thus to prepare 353 ml of a concentrated extraction solution. The concentration of the concentrated extract solution was 36.5 g/l.

The solution was rapidly frozen at −30° C. and then was kept under reduced pressure of 0.1 to 0.3 mmHg for 3 hours before the temperature reached the room temperature. By the freeze-drying, 1.10 g of brown powder was prepared. The powder was soluble in water with no restriction.

EXAMPLE 2 (Test)

The powder was dissolved in a double quantity of water to prepare a solution. The solution was used for the measurement of the infrared absorption spectrum thereof. The result of the measurement was as shown in FIG. 1.

Further, constituent matters contained in the powdered extract were measured by various methods. The results and measurement method were as follows:

| | | |
|---|---|---|
| Vitamin $B_{12}$ | 2.0 μg/10 g | Microorganism quantification method*) |
| Vitamin $B_2$ | 9.5 mg/10 g | Lumiflavin fluorescent luminous intensity method |
| Tannin | 2.5 g/10 g | FOLIN-DENIS method |

*Used bacteria stock: Lactobacillus leichmannii ATCC 7830.

Other constituent matters were not yet measured.

EXAMPLE 3 (Practical Use)

The results of the application to diabetic patients and liver dysfunction patients of the extract of the invention in the form of a diluted solution obtained by diluting the powder after the freeze-drying with a tenfold quantity of water are described hereunder.

a) A daily dosage of 1.5 g of the aforementioned diluted extract solution subdivided into 3 doses was administered to diabetic patients.

A first patient (female 40 years old) exhibited the blood sugar value of 166 mg/dl before administration. By administration, the blood sugar value of the patient was reduced to 142 mg/dl after 75 days, to 120 mg/dl after 90 days and to 110 mg/dl as a normal value (normal value: 60-110 mg/dl) after 130 days.

A second patient (female 52 years old) exhibited the blood sugar value of 204 mg/dl before administration. By administration, the blood sugar value of the patient was reduced to 166 mg/dl after 60 days, to 140 mg/dl after 75 days and to 106 mg/dl as a normal value after 90 days.

The blood sugar values (mg/dl) before dose and after 30 dose days for other patients are set forth in Table 1 (administration condition; as aforesaid):

TABLE 1

| | Patient Name | | | | | | | | | | | |
|---|---|---|---|---|---|---|---|---|---|---|---|---|
| | A | B | C | D | E | F | G | H | I | J | K | L |
| | ♂73* | ♂61 | ♂40 | ♂50 | ♂47 | ♂66 | ♀63 | ♂46 | ♀43 | ♂62 | ♂49 | ♀53 |
| before dose | 280 | 320 | 280 | 280 | 170 | 200 | 320 | 280 | 320 | 280 | 180 | 280 |
| after 30 dose day | 150 | 180 | 140 | 150 | 130 | 140 | 150 | 140 | 160 | 140 | 110 | 140 |

♂: male  ♀: female  *figures: age

| Test items | Dose days | Patient Name | | | | | | | |
|---|---|---|---|---|---|---|---|---|---|
| | | A ♀40 | B ♀28 | C ♀38 | D ♀70 | E ♂43 | F ♀52 | G ♀73 | H ♀58 |
| GOT | 0 | 58 | — | 60 | 49 | 50 | 60 | 60 | 75 |
| Normal | 60 | 55 | — | 35 | 28 | 30 | 55 | 47 | 78 |
| value: | 90 | 45 | — | — | 26 | 25 | 45 | — | 65 |
| not more than 40 | 100 | 36 | — | — | — | — | 35 | 39* | 50** |
| GPT | 0 | 45 | — | 50 | 40 | 45 | 55 | 51 | 55 |
| Normal | 60 | — | — | 30 | 28 | 35 | 50 | 37 | 55 |
| value: | 90 | 35 | — | — | 26 | — | 45 | — | 50 |
| not more than 35 | 100 | 29 | — | — | — | — | 35 | 31* | 40** |
| ZTT | 0 | — | — | 18 | — | 18 | — | 14.3 | — |
| Normal | 60 | — | — | 10.4 | — | 12 | — | 14.5 | — |
| value: | 90 | — | — | — | — | 4.3 | — | — | — |
| not more than 12 | 100 | — | — | — | — | — | — | 14.4* | — |
| ALP | 0 | — | 15 | — | 17.9 | 15 | — | 5.9 | — |
| Normal | 60 | — | 5.8 | — | 17.6 | 12 | — | 5.2 | — |
| value: | 90 | — | 5.5 | — | — | 6.1 | — | — | — |
| 3-11 | 100 | — | — | — | — | — | — | 6* | — |
| γ-G | 0 | — | — | 24 | — | — | 20 | 19.1 | 25 |
| Normal | 60 | — | — | 19 | — | — | 19 | 17.1 | 30 |
| value: | 90 | — | — | 16.2 | — | — | 18 | — | 20 |

TABLE 1-continued

| 9-18.5 | 100 | — | — | — | — | — | 16 | 16.8* | 17 |

*When the extract was administered by 150 days to the patient marked with *, the following effect was exhibited at the 150th day:
GOT 26
GPT 20
ZTT 11.7
ALP 4.8
Y-G 17.8

When the extract was administered by 150 days to the patient marked with , the following effect was exhibited at the 150th day:
GOT 40
GPT 32

It is apparent from the effects shown above that the extract according to the invention is very useful for the treatment for diabetes and liver dysfunction.

As described above, it is to be understood that the extract according to the present invention contains vitamin B12 which has been believed to be not present in plants, and that the extract exhibits the effect of a medicine for diabetic patients and liver dysfunction patients.

What is claimed is:

1. A process for reducing blood sugar values determined for a human suffering from diabetes, which comprises:
   systemically administering to said human a blood sugar reducing dose of a water-soluble extract from Pittosporaceae which exhibits the following characteristic absorption in the infra-red region of the spectrum:
   strong absorption bands at 1050–1070 cm$^{-1}$, and 3450 cm$^{-1}$; and
   relatively strong absorption bands at 520 cm$^{-1}$, 780 cm$^{-1}$, 1250 cm$^{-1}$, 1320 cm$^{-1}$ 1380–1440 cm$^{-1}$ (doublet), 1735 cm$^{-1}$ and 2850 cm$^{-1}$.

2. A process for normalizing liver function tests observed for humans suffering from liver dysfunctions, which comprises:
   systemically administering to said human a liver function normalizing dose of a water-soluble extract from Pittosporaceae which exhibits the following characteristic absorption in the infra-red region of the spectrum:
   strong absorption bands at 1050–1070 cm$^{-1}$, and 3450 cm$^{-1}$; and
   relatively strong absorption bands at 520 cm$^{-1}$, 780 cm$^{-1}$, 1250 cm$^{-1}$, 1320 cm$^{-1}$, 1380–1440 cm$^{-1}$ (doublet), 1735 cm$^{-1}$ and 2850 cm$^{-1}$.

* * * * *